United States Patent [19]

Itay

[11] Patent Number: 4,904,259
[45] Date of Patent: Feb. 27, 1990

[54] COMPOSITIONS AND METHODS FOR REPAIR OF CARTILAGE AND BONE

[76] Inventor: Samuel Itay, 16/3 Sharet St., Kfar-Saba, Israel, 44456

[21] Appl. No.: 280,122

[22] Filed: Dec. 5, 1988

Related U.S. Application Data

[63] Continuation-in-part of Ser. No. 187,730, Apr. 29, 1988.

[51] Int. Cl.$^4$ .......................... A61F 2/28; A61K 35/12
[52] U.S. Cl. .......................................... 623/16; 623/11; 623/66; 424/95; 530/838; 530/840; 514/2
[58] Field of Search ............... 530/810, 812, 830, 838, 530/840; 514/2; 424/9; 623/16, 66, 11, 15; 128/92 YR, 92 YG, 92 YQ, 92 W; 604/4, 7

[56] References Cited

U.S. PATENT DOCUMENTS 4,846,835  7/1989  Grande .............................. 623/16 X Primary Examiner—Alan W. Cannon
Attorney, Agent, or Firm—Merchant, Gould, Smith, Edell, Welter & Schmidt

[57] ABSTRACT

A defect is provided in cartilage or bone, or both, to excise damaged or pathological tissue, and it is filled with an implant having capability for complete regeneration of the skeletal tissue as a chondrogenic or osteogenic phenotype. The implant comprises cells expressing a chondrocyte phenotype ($80 \times 10^6$ cells/ml) embedded in a biocompatible matrix having about 20% serum, which provides a permissive environment for maturation and transformation of the implant to a fully integrated state with the surrounding tissue. A portion of the implant may comprise a bone segment or a bone substitute.

23 Claims, No Drawings

COMPOSITIONS AND METHODS FOR REPAIR OF CARTILAGE AND BONE

CROSS-REFERENCE

This is a continuation-in-part application of copending U.S. Serial No. 187,730, filed on April 29, 1988, pending, which is incorporated by reference herein.

BACKGROUND OF THE INVENTION

Compositions for use in repairing bone and cartilage by implantation of material comprising a proliferating chondrocyte cell structure having phenotypic capability embedded in a vehicle or gel consisting of thrombin, antiprotease, fibrinogen, extracellular matrix and one or more growth factors that forms a "biological glue" of a biodegradable character are described in U.S. Pat. No. 4,642,120. Before implantation, the cells are grown in tissue culture and harvested, and the chondrocyte population is embedded in the biological glue at a concentration of between from 100,000 to 500,000 cells per milliliter of glue. Before using this formulation, damaged cartilage and bone, as in a hip or other joint, are excised by surgery. A matching implant of the formulation is then inserted in the cavity, with or without bone segments to fill part of the volume. Cell proliferation continues in the permissive environment created by the system, while external influences are restricted. Chondrocytes (cartilage cells) and osteoblasts (bone forming cells) develop to unite with the existing structure, so that after a period of time, the implanted structure is virtually indistinguishable from the surrounding material.

Numerous advantages are derived from this approach in repair of articular cartilage, in comparison, for example, to replacement of a hip joint with a low friction metal-plastic prosthesis. The differences in the biomechanical properties between the bone and the prosthetic element is a major problem. Implantation of a prosthesis disables the mechanoreceptor system in the capsule of the joint which provides feedback for muscle control, resulting in wear and ultimately a need for replacement. The multiple freedoms of motion required of the joint, as for rotational and sliding movement, cannot be provided because of the absence of the mechanoreceptor system. In addition, the best low friction prosthetics have over 100 times the friction of the natural cartilage structure with the intervening synovial fluid, and for this reason also, wear and degradation are inevitable.

While the composition of U.S. Pat. No. 4,642,120 has a demonstrated potential for repair of articular cartilage, it also has been recognized to have a number of limitations as a result of further experimental work. The needed cell proliferation capability was thought to be best available in embryonal chondrocytes (young committed chondrocytes) but for human use, availability is limited and major problems can arise from immune system reactions. Bone marrow stem cells are merely mentioned in the patent as a different possible source of cells, along with mesenchyme cells having potentiality for conversion to cartilage cells by self differentiation or under the direction of chondrogenic factors. No work was done using these progenitors. Additional detailed information and discussion is contained in an article entitled "Use of Cultured Chick Epiphyseal Chondrocytes as Grafts for Defects in Chick Articular Cartilage", by S. Itay et al, *Clinical Orthopedics*, pp. 284-302, July, 1987.

The article mentioned cites a number of articles of general relevance to the topic as a whole. Three of these are of particular interest because they evidence attempts to transplant chondrocytes into articular cartilage that encountered limited success because, at least in part, of the absence of suitable biodegradable viscoelastic material and inability to produce cartilage. The three articles are: Bentley, G. et al, "Homotransplantation of isolated epiphyseal and articular cartilage chondrocytes onto joint surfaces of rabbits", *Nature* 230:385 (1971); Bentley, G. et al, "Isolated Epiphyseal chondrocyte allograft onto joint surface--An experimental study in rabbits", *Ann. Rheum. Dis.* 37:449 (1978); and Helbing, G. et al, "In vitro Untersuchungen an isolierten Chondrozyten zur Prognose von Knorpeltransplanten", *Helv. Chir. Acta* 46:21 (1979).

As pointed out in U.S. Pat. No. 4,642,120, it was previously thought that a limit had to be observed for chondrocyte concentrations of about 500,000 cells per milliliter of gel in order to avoid necrosis of the cells. Also, it was thought that only 5-50 units of thrombin per milliliter and about 25-80 mg/ml fibrinogen should be employed, with the setting of the gel being determined by the level of the thrombin, which should be kept at a limit of less than 50 units/ml. These relationships and parameters were found on further studies to limit proliferation rates and capacities, and capability for maturation and transformation of the implant into suitable phenotypic expressions, especially in large defects. Consequently, extension of this approach to repair of articular cartilage necessitates new compositions and procedures.

SUMMARY OF THE INVENTION

Compositions in accordance with the invention for regeneration of skeletal tissue employ cell cultures producing cells which express a chondrogenic phenotype. These include bone marrow derived chondrocytes and muscle fibroblast-derived chondrocytes as well as embryonal chondrocytes. Growth factors, mainly in the form of 10-20% serum, are employed in the culture medium to facilitate cell proliferation. A biological resorbable immobilization vehicle (BRIV) in the composition comprises about 15-30% serum, 100-150 mg/ml of fibrinogen, 60-90 units/ml thrombin, 60 mM calcium chloride ($CaCl_2$), and 2000 units/ml (KIU) aprotonin. The cells in the implant are at a concentration of $80-160 \times 10^6$ cells/ml of BRIV. The resultant composition enables cell proliferation at a higher rate in vivo, matures more quickly and transforms more readily into histological identity with surrounding cartilage and bone structures.

DETAILED DESCRIPTION OF THE INVENTION

The present invention is directed to a composition for use as an implant in the repair of defects in cartilage and bone. The compositions are prepared by the isolation of the suitable cells by trypsinization and disruption of the tissue. The cells are cultivated on a suitable medium, harvested, and are combined with a fibrinogen-based biological resorbable immobilization vehicle (BRIV). The BRIV gel composition with embedded cells can be utilized immediately, can be stored for limited periods of time (2-3 days) in an incubator, cryopreserved for up to 3 years, or the harvested cells can be preserved for long periods of time by deep freezing and thawing just before use and then be embedded in the desired gel composition. When the implant is to be utilized, the damaged cartilage and bone are excised by surgery, the gel is immersed in a solution of fibrinogen, the site of implantation is sprayed with a thrombin solution, and the gel implant is pressed into the defect or injured site.

The cells utilized are preferably bone marrow progenital cells, but embryonal cells and chondrocytes derived from muscle fibroblast or other mesenchyme originated cells can also be used. The bone marrow progenital cells or the muscle fibroblast derived chondrocytes afford the advantage that the patient himself can be the donor at a convenient early time, with less chance of an auto immune response.

Culturing the cells on plastic provides an adequate growth environment for cell proliferation and for the selection of the desired cell type. The culturing medium contains 10–20% fetal calf serum, and may optionally contain growth factors such as $IGF_I$, $IGF_{II}$, TGFB, PDGF, or any other growth factors that will be found to facilitate the proliferation of the cells. The cells are subcultured until pure fibroblast-like cell populations are achieved. The pure fibroblast-like cell populations are trypsinized and placed in a suspension culture at a density of $3-8 \times 10^6$ cells/ml of medium and are cultured above soft agar in a F-12 medium (Sigma Co.) with 10% fetal calf serum (F.C.S.) and 50 ug/ml of sodium ascorbate. After several days, the fibroblastic cells will be in aggregates of 30–60 cells.

Alternatively, the cells are trypsinized and the single cell suspension is cultured on Ham F-12 medium (Sigma Co.) on soft agar at a density of $2 \times 10^5$ to $4 \times 10$ cells/ml. 30–50 ug./cc of sodium ascorbate is added daily to the medium.

The cells which are used in the implant are embedded in a biological resorbable immobilization vehicle (BRIV), a viscoelastic, biodegradable, biocompatible, resorbable matrix, at a concentration of $80-160 \times 10^6$ cells/ml of BRIV. The BRIV composition provides good adhesion and selective permeability of nutritive liquids and trophic agents. The BRIV gel also mechanically prevents cell migration. In addition, apart from fixing the chondroycytes in the defect sites, the BRIV also serves effectively as a proper extracellular milieu, supporting the growth and the differentiated state of the chondroycytes, while preventing fibroblast penetration and proliferation.

The composition of the BRIV comprises about 15–30% serum, 100–150 mg/ml of fibrinogen, 60–90 units/ml thrombin, 60mM calcium chloride ($CaCl_2$), and an antiprotease, such as aprotonin. Preferably, the BRIV implant composition comprises 20% fetal calf serum, 150 mg/ml fibrinogen, 90 units/ml of thrombin in 60mM of $CaCl_2$, and 2000 units/ml (KIU) aprotonin. The serum utilized in the BRIV can be fetal calf serum, umbilical cord serum from the second trimester, or horse serum, although fetal calf serum is preferred. Generally, a natural non-plasma protease inhibitor is used to prevent fast lysis of the matrix. A combination of polysaccharide inhibitors with plasma protease inhibitors and/or synthetic protease inhibitors can be used. Suitable protease inhibitors are chemical inhibitors such as epsilon-aminocaproic acid used in quantities of about 200–400 mg/ml of gel, and tranexemic acid, used in quantities of about 200–400 mg/ml of gel. Polysaccharide inhibitors can also be used. Also, a natural non-plasma protease inhibitor such as anti-trypsin (Chicken egg white, Sigma, type III) may be used or suitable synthetic protease inhibitors. Plasma protease inhibitors may also be utilized.

The bioimplants of the invention can be utilized in various ways. A freshly prepared implant (BRIV composition containing embedded cells) can be applied directly to the injured site or defect. In addition, the BRIV composition with embedded cells can be covered with F-12 medium (Sigma Company) plus 10% fetal calf serum and can be stored in a $CO_2$ incubator for a 2–3 days, at about 37° C. Further, an implant can be prepared from cryopreserved cells (90% fetal calf serum and 10% DMSO) in liquid nitrogen (cryopreserved for up to 3 years) which have been thawed and then embedded in BRIV. As a preferable option, the cells can be collected by centrifugation, and the complete implant with cells embedded in BRIV can be cryopreserved (90% fetal calf serum and 10% dimethyl sulfoxide (DMSO)) in liquid nitrogen for longer periods. The implant in this case is thawed in the operating room and immediately implanted. An implant may optionally contain bone segments or bone substitute to fill part of the volume.

When the implant is to be utilized, the injured site or defect is sprayed with a thrombin solution, and the BRIV matrix containing cells is immersed in a solution containing fibrinogen and antiprotease. The implant is pressed into the injured site or defect so as to fill up the defect. The thrombin solution comprises 90 units/ml thrombin in 60mM $CaCl_2$.

Within 48 hours after implantation, chondrocyte proliferation is seen. Two weeks later, hyaline cartilage matrix surrounds these cells. Within eight weeks, the defects are completely filled with hyaline cartilage which integrates smoothly with the neighboring cartilage without the formation of fibrous tissue at the interface. The cell content and the rate of proteoglycan synthesis in the reparative tissue remains high for four months, then declines slowly towards the level of the surrounding cartilage. Six months after transplantation, the cartilaginous repair tissue at the level below the ossification front shows penetration by vascular elements and cartilage to bone transformation. Eighteen months after transplantation, all the implant below the ossification front transforms into bony elements, while the articular part of the implant remains cartilaginous with all the properties of the orignial cartilage. No signs of immunogenic rejection or degenerative changes of the implant are observed. On the contrary, the articular surface of the implanted area appears to be younger than the original surface.

The composition of the invention permits cell proliferation at a higher rate in vivo. The cells in the implant mature more quickly, and transform more readily into histological identity with the surrounding cartilage and bone structures. Within two months of transplantation, the defect is filled properly with active proliferating cells, and is integrated well with no fibrocartilage or other soft tissue at the edges. At 2 to 6 months, all the implant that is below the osteochondral junction is transformed into bone while articular cartilage retains its cartilagineous properties. The biodegradable BRIV of the implant has been reabsorbed.

The following specific Examples can be used to further illustrate the invention which contain a best mode. The Examples were prepared and tested as described.

EXAMPLE 1

Implant Containing Bone Marrow Derived Chondrocytes

Autologous or homologous bone marrow is obtained by aspiration with a bone biopsy needle from the iliac crest or femoral canal. The aspirated cells are injected into phosphate buffered saline (PBS) containing 0.25% trypsin and injected sequentially through 17, 18 and 20 gauge needles to achieve a single cell suspension. Higher gauge needles are found to induce some cell destruction. The cells are plated at a density of $50-100\times10^6$ cells on 100 mm tissue culture dishes fed with $BGJ_b$ medium (GIBCO) with 15% F.C.S. The medium is changed daily or as required by the proliferation rate of the cells. The medium may be supplemented by growth factors such as $IGF_I$, $IGF_{II}$, TGFB, PDGF or any other growth factors that will be found to facilitate the proliferation of the cells. The cells are subcultured weekly and after 5-6 subculturings, an almost pure fibroblastic stromal cell population is achieved. This cell population is then trypsinized and put in a suspension culture at a density of $3-8\times10^6$ cells/ml of medium and cultured above soft agar in a F-12 medium (Sigma Co.) with 10% F.C.S. and 50 ug/ml sodium ascorbate added daily to the medium. The fibroblastic stromal cells start to aggregate immediately and after three-seven days, most of the cells are in aggregates of 30-60 cells. All the aggregates express a chondrogenic phenotype, as determined by employing histochemical and immunohistochemical probes for analysis.

Although bone marrow derived chondrocytes are preferred in this example, one can use chondrocytes or osteoblasts of autologous or homologous origin, or homologous committed chondrocytes, or any other progenital cells of mesenchymal origin. It can be seen that this initial formulation comprises purification, proliferation and manipulation of a population expressing a chondrogenic or osteogenic phenotype. More specifically, the proliferating cells are from the class comprising bone marrow stroma cells, embryonal committed chondrocytes and any undifferentiated mesenchymal cells.

To incorporate the cells in a biodegradable viscoelastic matrix, the resulting pellet of cells is resuspended in a small volume of phosphate buffer saline (PBS) containing fibrinogen (150 mg/ml) and 20% of fetal calf serum and aprotonin, available under the trademark "Trasylol" (2000 KIU/ml) or another antiprotease. The solution contains cells (ranging in concentration between $80-160\times10^6$ cells/ml), fibrinogen, 15-30% serum and antiprotease and may be designated solution A. Specifically in this example $120\times10^6$ cells/ml of BRIV, 20% fetal calf serum, 150 mg/ml fibrinogen, 90 units/ml of thrombin in 60 mM $CaCl_2$, and 2,000 units of aprotonin are employed. A second solution, designated as solution B, comprises thrombin (90 units/ml in 60 mM CaCl). The solutions are mixed, keeping the ratio of solutions A and B 3:1 (v/v). The implant is immersed in F-12 medium containing 10% F.C.S. and may be immediately used. Alternatively, the implant may be cryopreserved (in $LN_2$, for example) in 90% F.C.S. and 10% DMSO (or any other cryopreservation regime). At transplantation, the defect is sprayed with a thrombin solution and the implant is press fitted into the defect.

Data collected in experimentation with bone marrow derived chondrocytes and embryonal derived chondrocytes in several species (avian and mammalian) by macroscopic observation, histological sections, and biochemical test showed that at the site of transplantation within two months the defect is filled properly with a complete congruency at the articular surface and perfect integration with no fibrocartilage or other soft tissue at the interfaces. At 2 to 6 months all the implant that is below the osteochondral junction is transformed into bone while articular cartilage retains its cartilagineous properties. No degenerative changes or immunological rejection is observed after prolonged follow-up periods.

Although the serum is preferentially fetal calf serum in this example, umbilical cord serum from the second trimester or horse serum or any combination of these may be employed. No extracellular matrix need be used.

EXAMPLE 2

Preparation of Composition for Cartilage Repair

As starting material, epiphysis of long bones (tibia, femur, humerus) was used. The isolation procedure of embryonal chondrocytes comprises trypsinization of the epiphysis (1% porcine trypsin), incubation for 60 minutes at 37° C. and vortexing for 2 minutes in each 10 minute interval and thereafter a gentle mechanical disintegration of the tissue by a Teflon channeled homogenizer. Trypsin activity is terminated by serum which contains an antiproteolytic substance. The resulting single cell suspension is then seeded for several days (4-7 days) in Ham F-12 medium (Sigma Co.) on plates coated with soft agar (0.5% Bacto-agar in Ham F-12) at a density of $2\times10^5$ to $4\times10^5$ cells/ml. An amount of 50 ug of sodium ascorbate is added daily to the medium. During this growth period, most of the fibroblasts are dying off and chondrocyte enrichment does occur. The cells are collected by centrifugation and used directly in the BRIV as a fresh graft. Alternatively, the complete graft may be cryopreserved, or the cells may be cryopreserved (90% fetal calf serum (F.C.S.) and 10% dimethyl sulfoxide (DMSO)) in liquid nitrogen for longer periods and embedded at a later date in BRIV. The cells were collected and embedded at a concentration of $80-160\times10^6$ cells/ml of the same viscoelastic biodegradable matrix as in Example 1. The results obtained are comparable to those of Example 1.

EXAMPLE 3

Implant Containing Muscle Fibroblast-Derived Chondrocytes

Autologous or homologous muscle is obtained by an open biopsy under local anesthesia. The muscle is minced into very small pieces of tissue and is then trypsinized for 30 minutes in 0.5% trypsin in P.B.S. and Ethylene Diamine Tetraacetic Acid (E.D.T.A.) with occasional vortexing. The trypsinized cells are then filtered through a 53 micron Nitex filter. The trysinization is then stopped by M.E.M. (minimal essential) medium (GIBCO Co.) containing 15% F.C.S. After centrifugation, the pellet of cells is washed with M.E.M. medium containing 15% F.C.S. The cells are then plated at a density of $50-100\times10^6$ cells per 100 mm tissue culture dishes and are maintained daily with M.E.M. medium with 15% F.C.S. The cells are subcultured weekly on M.E.M. medium with 15% F.C.S. and after three subculturings, a pure fibroblastic-like population is achieved. This cell population is then trypsinized and put in a suspension culture at a concentration of $3-8 \times 10^6$ cells/ml. of medium and cultured above soft agar in F-12 medium (Sigma Co.) with 10% F.C.S. and 50 ug/ml of sodium ascorbate added daily to the medium. The fibroblastic cells start to aggregate immediately and after three to seven days most of the cells are in aggregates of 30-60 cells. All the aggregates express a chondrogenic phenotype as determined by employing histochemical and immunohistochemical probes for analysis.

Although muscle-derived chondrocytes are preferred in this example, one can use bone marrow-derived chondrocytes or committed chondrocytes as well. The cells are collected by centrifugation and directly embedded at a concentration of $80-160 \times 10^6$ cells/ml of the same viscoelastic biodegradable matrix (BRIV) as in Example 1. Alternatively, the cells can be cryo-preserved (in 90% F.C.S. and 10% DMSO) in liquid nitrogen for long periods, thawed before usage, embedded in BRIV at a concentration of $80-160 \times 10^6$ cells/ml and used. As a further alternative, the cells can be embedded in BRIV, with the entire implant being cryo-preserved in 90% F.C.S. and 10% DMSO, and thawed before usage in the operating room. The results obtained are comparable to those of Example 1.

EXAMPLE 4

Preparation of Composition for Bone Repair

In order to regenerate bone defects, one of three methods may be used.

4A. For small defects 2-4 cm in length, one uses an implant as proposed in Example 1, Example 2, or Example 3.

4B. For large defects, a composition graft of bone substitute used as a supporting matrix with biomechanical properties near to the properties of a native bone is used. The cells are combined with this matrix via the biodegradable fibrinogen based adhesive matrix.

4C. The bone marrow stromal cells can be induced in vitro to express an osteoblastic phenotype and used directly as in 4A or 4B to correct bony defects. (This can be used only in the autologous group where the bone marrow originates from the patient with the bone defect.)

The Process

A traumatic (fracture) or pathologic (tumor) or degenerative disease defect in bone or articular cartilage is cleaned up and shaped into geometric configuration (cuboidal or cylindrical). In the case of an articular surface, the entire procedure can be done through an arthroscopic device.

After the damaged area is prepared, a frozen implant with an identical shape (prepared as described in detail in Example 1, Example 2 or Example 3) is rapidly thawed by putting it into saline at 37° C. for 5-10 minutes.

The implant is then immersed in a solution of fibrinogen and the implantation site is sprayed with the thrombin solution. The implant is now press fitted into the defect. In an articular defect, continuous passive motion is started immediately.

In the case of large defects, a composite graft of the biological implant embedded in (or above) a bone substitute material of suitable shape can be used. This implant will be either custom made or as a commercial standard type.

While various alternatives and modifications are proposed above, it will be appreciated that the invention is not limited thereto but encompasses all forms and variations in accordance with the appended claims.

I claim:

1. A method of regenerating skeletal tissue of a subject comprising the steps of:
    a. culturing a proliferating cell population comprising autologous bone marrow stroma cells;
    b. manipulating them in suspension above soft agar at a concentration in excess of $2 \times 10^6$ cell/ml of medium for at least five days;
    c. harvesting the cells;
    d. embedding the cells at a concentration in excess of $80 \times 10^6$ cells/ml of a biological resorbable immobilization vehicle (BRIV) including in excess of 10% serum, 100 mg/ml fibrinogen, and 60 units/ml thrombin in an excess of 40mM $CaCl_2$ and 2,000 units of aprotonin;
    e. removing a damaged part of the subject's skeletal tissue to leave a clean geometric shaped defect; and
    f. filling the defect with an implant at least including the combined cell concentration and BRIV.

2. The method as set forth in claim 11 above, wherein the BRIV includes 15-30% serum and 60 units/ml thrombin in an excess of 60mM $CaCl_2$.

3. The method as set forth in claim 1 above, wherein the biological implant is stored under low temperature conditions after preparation with a preservative medium containing 90% F.C.S. and 10% DMSO, and wherein there is about 20% serum.

4. The method as set forth in claim 1 above, wherein the harvested cells are stored under low temperature conditions after preparation with a preservative medium containing 90% F.C.S. and 10% DMSO, and embedded at a later date in BRIV.

5. The method as set forth in claim 1 above, wherein the skeletal tissue to be repaired comprises articular cartilage and the joint operated on is subjected to a continuous passive motion after implantation.

6. The method according to claim 1, wherein the serum is selected from the group consisting of fetal calf serum, umbilical cord serum from the second trimester, and horse serum.

7. A method of regenerating skeletal tissue of a subject, comprising the steps of:
    a. culturing a proliferating cell population comprising autologous muscle fibroblast derived chrondocytes;
    b. manipulating the cells in suspension and culturing the cells above soft agar at a concentration in excess of $2 \times 10^6$ cells/ml of medium for at least 3 days;
    c. harvesting the cells;
    d. embedding the cells at a concentration in excess of $80 \times 10^6$ cells/ml of a biological resorbable immobilization vehicle (BRIV), the BRIV comprising in excess of 10% serum, 100 mg/ml fibrinogen, 60 units/ml thrombin in an excess of 40mM $CaCl_2$, and 2000 units of aprotonin;
    e. removing a damaged part of the subject's skeletal tissue to leave a clean geometric shaped defect; and
    f. filling the defect with an implant at least including the combined cell concentration and BRIV.

8. The method of claim 7 as set forth above, wherein the BRIV includes 15-30% serum and 60 units/ml thrombin in an excess of 60mM $CaCl_2$.

9. The method as set forth in claim 7, wherein the biological implant is stored under low temperature conditions after preparation with a preservative medium containing 90% FCS and 10% DMSO, and wherein there is about 20% serum.

10. The method as set forth in claim 7 above, wherein the harvested cells are stored under low temperature conditions after preparation with a preservative medium containing 90% FCS and 10% DMSO, and embedded at a later date in BRIV.

11. The method as set forth in claim 7 above, wherein the skeletal tissue to be repaired comprises articular cartilage and bone.

12. A method of regenerating skeletal tissue in a person, comprising the steps of:
   a. obtaining a bone marrow sample from a donor;
   b. culturing a proliferative cell population comprising bone marrow osteogenic-chondrogenic progenitor cells;
   c. harvesting the cells;
   d. manipulating the cells in suspension above soft agar at a concentration in excess of $2 \times 10^6$ cells/ml of medium for at least five days;
   e. embedding the cells at a concentration in excess of $80 \times 10^6$ cells/ml of a biological resorbable immobilization vehicle (BRIV) including in excess of 10% serum, 100 mg/ml fibrinogen and 60 units/ml thrombin in 60 mM $CaCl_2$ and 2000 units of aprotonin;
   f. removing a damaged part of the person's skeletal tissue to leave a clean geometric shaped defect; and
   g. filling the defect with an implant at least including the combined cell concentration and BRIV.

13. The method of claim 12 wherein the bone marrow sample is obtained by aspiration from the iliac crest of the donor.

14. The method of claim 12 wherein the donor of the bone marrow sample and the person receiving the implant are the same person.

15. The method as set forth in claim 12 above wherein the BRIV includes 15-30% serum and 60 units/ml thrombin in an excess of 60 mM $CaCl_2$ and 2000 units of aprotonin.

16. The method as set forth in claim 12 above, wherein the biological implant is stored under low temperature conditions after preparation with a preservative medium containing 90% F.C.S. and 10% DMSO.

17. The method as set forth in claim 12 above, wherein the harvested cells are stored under low temperature conditions after preparation with a preservative medium containing 90% F.C.S. and 10% DMSO, and embedded at a later date in BRIV.

18. The method as set forth in claim 12 above, wherein the skeletal tissue to be repaired comprises articular cartilage and the joint operated on is subjected to a continuous passive motion after implantation.

19. The method according to claim 12, wherein the serum is selected from the group consisting of fetal calf serum, umbilical cord serum from the second trimester, and horse serum.

20. The method as set forth in claim 12 wherein the cells and the BRIV are embedded in a suitably shaped biodegradable bone substitute.

21. The method as set forth in claim 12 above wherein the concentration of the cells is between $80 \times 10^6$ cells/ml and $160 \times 10^6$ cells/ml BRIV.

22. The composition of claim 12, wherein the protease inhibitor is selected from the group consisting of polysaccharides, plasma protease, synthetic and natural non-plasma protease inhibitors.

23. The method as set forth in claim 12 wherein the cells originate from a nonhuman source.

* * * * *